(12) United States Patent
Liu

(10) Patent No.: US 8,993,292 B2
(45) Date of Patent: Mar. 31, 2015

(54) METHODS AND SYSTEMS FOR DIFFERENTIAL EXTRACTION

(75) Inventor: Yingjie Liu, Foster City, CA (US)

(73) Assignee: Applied Biosystems LLC, Carlsbad, CA (US)

( * ) Notice: Subject to any disclaimer, the term of this patent is extended or adjusted under 35 U.S.C. 154(b) by 1409 days.

(21) Appl. No.: 12/117,579

(22) Filed: May 8, 2008

(65) Prior Publication Data

US 2008/0281089 A1   Nov. 13, 2008

Related U.S. Application Data

(60) Provisional application No. 60/916,999, filed on May 9, 2007.

(51) Int. Cl.
*C12N 13/00* (2006.01)
*C12N 15/10* (2006.01)
*C12N 1/06* (2006.01)
*C12M 1/34* (2006.01)

(52) U.S. Cl.
CPC ............ *C12N 15/1006* (2013.01); *C12N 13/00* (2013.01); *C12M 41/46* (2013.01); *C12N 1/066* (2013.01)
USPC ..................................... 435/173.1; 435/306.1

(58) Field of Classification Search
CPC .......... C12M 1/33; C12M 47/06; C12M 1/42; C12N 1/066; C12N 13/00; C12N 1/16; C12N 15/1003; C12N 15/1006; C12N 15/101; B01L 2400/0487; A61K 41/0004; A61K 36/06; A61K 37/70; A23L 1/3016; C12Q 1/6806
USPC ......................... 435/173.1, 306.1; 536/25.41
See application file for complete search history.

(56) References Cited

U.S. PATENT DOCUMENTS

| 5,541,072 A | 7/1996 | Wang et al. |
| 6,368,800 B1 | 4/2002 | Smith et al. |
| 2003/0038087 A1 | 2/2003 | Garvin |
| 2005/0019905 A1* | 1/2005 | Larson et al. ............ 435/297.5 |
| 2005/0032097 A1 | 2/2005 | Garvin |

FOREIGN PATENT DOCUMENTS

| WO | WO-00/77251 | 12/2000 |
| WO | WO-01/12847 | 2/2001 |
| WO | WO-03/070898 | 8/2003 |
| WO | WO-2006/031591 | 3/2006 |
| WO | WO-2008/089280 | 7/2008 |

OTHER PUBLICATIONS

Technical Bulletin: DNA IQ (TM) Casework Sample Kit for Maxwell 16. Promega. Revised Oct. 2008.*
International Congress Series, vol. 1288, pp. 700-703 (2006).
Forensic Science International, vol. 72, pp. 25-33 (1995).
Legal Medicine, vol. 8, pp. 43-47 (2006).

(Continued)

*Primary Examiner* — Michael Hobbs

(57) ABSTRACT

Methods are provided for differential extraction of DNA from at least two different cell types. Systems for carrying out the differential extraction methods are also provided. A kit is also provided for differential extraction of DNA from at least two different cell types using a multi-compartment container.

18 Claims, 3 Drawing Sheets

| Magnetic Bar | Cell-trapping matrix | 1 |
|---|---|---|
| | Cell wash buffer | 2 |
| | Selective sperm lysis buffer | 3 |
| Magnetic Bar | Dilution buffer + DNA-binding particles | 4 |
| | DNA wash buffer | 5 |
| | Elution buffer | 6 |

| Waste | 0 |
|---|---|

(56) References Cited

OTHER PUBLICATIONS

International Search Report for Int'l appl. No. PCT/US08/063273 dated Sep. 3, 2008. Along with the Written Opinion of the International Searching Authority.
EZ1 DNA Handbook, Second Edition, Feb. 2004, 24 pages, www.giagen.com.
Maxwell® 16 System datasheet, www.promega.com/maxwell16/dnaiq/, 4 pages, first available Nov. 15, 2006.
Maxwell™ 16 datasheet, Profiles in DNA, Feb. 2006, www.promega.com, 3 pages.
Garvin, A. M., "Filtration Based DNA Preparation for Sexual Assault Cases", *Journal of Forensic Sciences, Callaghan and CO, Chicago* vol. 48, No. 5, Sep. 1, 2003, 1084-1087.
Gill, P. et al., "Forensic Application of DNA 'Fingerprints' Nature", *Nature Publishing Group,London*, vol. 318 No. 6046 pp. 577-578 Dec. 12, 1985.
Extended European Search Report for EP Application No. 08755249.3, dated Jun. 25, 2010.
Written Opinion and International Preliminary Report on Patentability for PCT Application No. PCT/US2008/063273, mailed Nov. 19, 2009.

\* cited by examiner

FIGURE 1

| Magnetic Bar | Cell-trapping matrix | 1 |
| --- | --- | --- |
| | Cell wash buffer | 2 |
| | Selective sperm lysis buffer | 3 |
| Magnetic Bar | Dilution buffer + DNA-binding particles | 4 |
| | DNA wash buffer | 5 |
| | Elution buffer | 6 |

| Waste | 0 |
| --- | --- |

FIGURE 2

| Magnetic Bar | Cell-trapping matrix | 1 |
| --- | --- | --- |
| | Cell wash buffer | 2 |
| | Selective sperm lysis buffer | 3 |
| | DNA-binding buffer | 4 |
| Magnetic Bar | Dilution buffer + DNA-binding particles | 5 |
| | DNA wash buffer | 6 |
| | Elution buffer | 7 |

| Waste | 0 |
| --- | --- |

FIGURE 3

| Magnetic Bar | Cell-trapping matrix | 1 |
| --- | --- | --- |
|  | Cell wash buffer | 2 |
|  | Selective sperm lysis buffer | 3 |
| Magnetic Bar | DNA-binding buffer +DNA-binding particles | 4 |
| Magnetic Bar | Dilution buffer + DNA-binding particles | 5 |
|  | DNA wash buffer | 6 |
|  | Elution buffer | 7 |

| Waste | 0 |
| --- | --- |

FIGURE 4

| Magnetic Bar | Cell-trapping matrix | 1 | | | |
| --- | --- | --- | --- | --- | --- |
| Magnetic Bar | Cell wash buffer | 2 | | | |
| Magnetic Bar | Selective sperm lysis buffer | 3 | DNA-binding buffer | 7 | Magnetic Bar |
| Magnetic Bar | Dilution buffer + DNA-binding particles | 4 | DNA wash buffer | 8 | Magnetic Bar |
| Magnetic Bar | DNA wash buffer | 5 | Elution buffer | 9 | Magnetic Bar |
| Magnetic Bar | Elution buffer | 6 | | | |

FIGURE 5

| Magnetic plunger | Cell-trapping matrix | | | 1 | |
|---|---|---|---|---|---|
| Magnetic plunger | Cell wash buffer | | | 2 | |
| Magnetic plunger | Selective sperm lysis buffer | 3 | DNA-binding buffer | 6 | Magnetic plunger |
| Magnetic plunger | Dilution buffer + DNA-binding particles | | | | |
| Magnetic plunger | DNA wash buffer | | 4 | DNA wash buffer | 7 | Magnetic plunger |
| Magnetic plunger | Elution buffer | | 5 | Elution buffer | 8 | Magnetic plunger |

FIGURE 6

| Magnetic plunger | Cell-trapping matrix | | | 1 | |
|---|---|---|---|---|---|
| Magnetic plunger | Cell wash buffer | | | 2 | |
| Magnetic plunger | Selective sperm lysis buffer | 3 | General lysis buffer | 7 | Magnetic plunger |
| Magnetic plunger | Dilution buffer | | DNA-binding buffer | | |
| Magnetic plunger | DNA-binding particles | 4 | DNA wash buffer | 8 | Magnetic plunger |
| Magnetic plunger | DNA wash buffer | 5 | Elution buffer | 9 | Magnetic plunger |
| Magnetic plunger | Elution buffer | 6 | | | |

METHODS AND SYSTEMS FOR DIFFERENTIAL EXTRACTION

CROSS REFERENCE TO RELATED APPLICATIONS

This application claims the benefit of U.S. Provisional Application No. 60/916,999 filed May 9, 2007, and is related to U.S. Provisional Application No. 60/880,787 filed Jan. 16, 2007, U.S. Provisional Application No. 60/899,106 filed Feb. 2, 2007, U.S. patent application Ser. No. 12/015,414 filed Jan. 16, 2008, and U.S. patent application Ser. No. 12/032,270 filed Feb. 15, 2008. The disclosures of the above applications are incorporated by reference in their entirety.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

FIELD

Methods are provided for differential extraction of DNA from at least two different cell types. Systems for carrying out the differential extraction methods are also provided.

BACKGROUND OF THE INVENTION

Forensic DNA analysis of sexual assault evidence often involves analysis of DNA from sperm cells and DNA from other cells such as epithelial cells. The samples obtained from victims often contain a mixture of sperm and other cells such as epithelial cells. Because other cells such as epithelial cells may outnumber sperm cells by many folds, contamination from one or more other sources of DNA may occur while sperm DNA is being extracted. Therefore, it is often desirable to separate the sperm cells and epithelial cells, or separate the sperm DNA from the epithelial DNA as much as possible, prior to analysis. In certain instances, separation and isolation of a particular DNA to create an accurate profile is important for identification of an assailant.

Differential extraction is a broad term used to describe several extraction methods that can be used to separate cells. In certain instances, unique characteristics of sperm cells allow for the differential extraction of the epithelial cells from the sperm cells. One differential extraction procedure was described in 1985 (Gill et al., (1985) Nature 318: 557-9). In certain instances, separation of the sperm cell fraction from the victim's DNA profile decreases ambiguity in the results and allows for easier interpretation of the perpetrator's DNA profile in a rape case.

SUMMARY OF THE INVENTION

In certain embodiments, a system for differential extraction of sperm cells is provided. In certain embodiments, the system comprises a plurality of compartments, wherein at least one compartment comprises a selective sperm lysis buffer. In certain embodiments, the system comprises a first compartment comprising a cell-trapping matrix and a second compartment comprising a selective sperm lysis buffer. In certain embodiments, the system further comprises a third compartment comprising a plurality of DNA-binding particles. In certain embodiments, the system further comprises a fourth compartment comprising an elution buffer.

In certain embodiments, a system for differential extraction of sperm cells comprises a first compartment comprising a cell-trapping matrix; a second compartment comprising a cell wash buffer, a third compartment comprising a selective sperm lysis buffer; a fourth compartment comprising a plurality of DNA binding particles; a fifth compartment comprising a DNA wash buffer; and a sixth compartment comprising an elution buffer. In certain embodiments, the system further comprises a seventh compartment comprising a DNA-binding buffer. In certain embodiments, the seventh compartment further comprises a second plurality of DNA-binding particles. In certain embodiments, the system further comprises an eighth compartment comprising a second plurality of DNA-binding particles.

In certain embodiments, the system comprises a plurality of compartment, wherein the plurality of compartments are part of a removable cartridge.

In certain embodiments, a method of differential extraction of sperm cells in a biological sample that comprises sperm cells and non-sperm cells is provided. In certain embodiments, the method comprises (a) placing the biological sample in a first compartment of a system, wherein the first compartment comprises a cell-trapping matrix; (b) capturing the sperm cells and the non-sperm cells with the cell-trapping matrix; (c) incubating the cell-trapping matrix and the captured sperm cells and non-sperm cells in a selective sperm lysis buffer to form a sperm cell lysate; (d) binding sperm cell DNA from the sperm cell lysate to a plurality of DNA-binding particles; and (e) eluting the sperm cell DNA from the DNA-binding particles.

In certain embodiments, capturing the sperm cells and the non-sperm cells with the cell-trapping matrix comprises applying a magnetic force to the cell-trapping matrix. In certain embodiments, incubating the cell-trapping matrix and the captured sperm cells and non-sperm cells in a selective sperm lysis buffer occurs in the first compartment of the system. In certain embodiments, the binding the sperm cell DNA to a plurality of DNA-binding particles occurs in a second compartment of the system. In certain embodiments, eluting the sperm cell DNA from the DNA-binding particles occurs in the second compartment of the system. In certain embodiments, the sperm cell lysate is moved from the first compartment to the second compartment.

In certain embodiments, incubating the cell-trapping matrix and the captured sperm cells and non-sperm cells in a selective sperm lysis buffer occurs in a second compartment of the system. In certain embodiments, binding the sperm cell DNA to a plurality of DNA-binding particles occurs in a second compartment of the system. In certain embodiments, eluting the sperm cell DNA from the DNA-binding particles occurs in a third compartment of the system. In certain embodiments, the cell-trapping matrix and the captured sperm cells and non-sperm cells are moved from the first compartment to the second compartment using a magnetic force.

In certain embodiments, the non-sperm cells remain captured on the cell-trapping matrix after incubating the cell-trapping matrix in the selective sperm lysis buffer. In certain embodiments, the non-sperm cells are lysed and the non-sperm cell DNA is bound to the cell-trapping matrix. In certain embodiments, the non-sperm cells are lysed and the non-sperm cell DNA is bound to a second plurality of DNA-binding particles.

DESCRIPTION OF THE FIGURES

The skilled artisan will understand that the Figures, described below, are for illustration purposes only. The drawings are not intended to limit the scope of the claimed invention in any way.

FIG. 1 shows an exemplary system for differential extraction of sperm cell DNA and non-sperm cell DNA according to certain embodiments. The system of FIG. 1 involves transfer of fluids between compartments. The system of FIG. 1 does not lyse the non-sperm cells, but instead collects residual DNA present in the sample after cell capture on the cell-trapping matrix.

FIG. 2 shows an exemplary system for differential extraction of sperm cell DNA and non-sperm cell DNA according to certain embodiments. The system of FIG. 2 involves transfer of fluids between compartments. The system of FIG. 2 uses the cell-trapping matrix as the DNA-binding particles for the non-sperm cell DNA.

FIG. 3 shows an exemplary system for differential extraction of sperm cell DNA and non-sperm cell DNA according to certain embodiments. The system of FIG. 3 involves transfer of fluids between compartments. The system of FIG. 3 comprises two separate compartments of DNA-binding particles.

FIG. 4 shows an exemplary system for differential extraction of sperm cell DNA and non-sperm cell DNA according to certain embodiments. The system of FIG. 4 involves the transfer of particles and, in some instances, liquid between compartments. The cell-trapping matrix is used as the DNA-binding matrix for the non-sperm cell DNA in the system shown in FIG. 4.

FIG. 5 shows an exemplary system for differential extraction of sperm cell DNA and non-sperm cell DNA according to certain embodiments. The system of FIG. 5 involves the transfer of particles between compartments. The cell-trapping matrix is used as the DNA-binding matrix for the non-sperm cell DNA in the system shown in FIG. 5.

FIG. 6 shows an exemplary system for differential extraction of sperm cell DNA and non-sperm cell DNA according to certain embodiments. The system of FIG. 6 stores the DNA-binding particles separately from the DNA-binding buffer.

DESCRIPTION OF VARIOUS EMBODIMENTS

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in this application, this application controls.

The use of the singular includes the plural unless specifically stated otherwise. The word "a" or "an" means "at least one" unless specifically stated otherwise. The use of "or" means "and/or" unless stated otherwise. The use of "or" in the context of multiply dependent claims means the alternative only. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

In this specification, discussion of detecting "a" moiety, such as a target analyte, encompasses one or more of that moiety unless specifically stated otherwise. All ranges discussed herein include the endpoints and all values between the endpoints.

DEFINITIONS

The term "biological sample" refers to any sample that contains at least one biological material. Exemplary biological materials include, but are not limited to, blood, saliva, skin, feces, urine, sperm cells, epithelial cells (including, but not limited to, vaginal epithelial cells), muscle tissue, and bone.

The term "cartridge" refers to a system that comprises a plurality of compartments and does not contain sufficient fluid and/or magnetic particle handling mechanisms to function independently of a separate fluid-handling and/or magnetic particle-handling instrument. A cartridge may be, in certain embodiments, designed for a single use, after which it is discarded. In certain embodiments, one or more of the compartments in a cartridge contains a reagent. In certain embodiments, all of the compartments of a cartridge are contained in a single unit. In certain embodiments, the compartments of a cartridge are divided between two or more units that together form the cartridge. In various embodiments, a single cartridge is designed to process 1, 2, 4, 6, 8, 12, 16, 24, 48, 96 or more than 96 samples. In various embodiments, a cartridge is designed to process between 1 and 48 samples, or between 1 and 24 samples, or between 2 and 24 samples, or between 1 and 16 samples, or between 2 and 16 samples. In certain embodiments, when a cartridge is designed to process at least two samples, it is designed to process at least two of the samples simultaneously. In certain embodiments, a cartridge is designed to process all of the samples simultaneously.

The term "cell mixture" refers to a heterogeneous collection of at least two or more different cell types.

The term "cell-trapping matrix" refers to a matrix that captures cells, including but not limited to, sperm cells and epithelial cells. Certain exemplary cell trapping matrices are described, e.g., in U.S. Provisional Application No. 60/890,460. In certain embodiments, a cell-trapping matrix captures cells but does not bind DNA in the presence of a cell wash buffer, but is capable of binding DNA in a DNA-binding buffer.

The term "cell wash buffer" refers to a buffer in which cells are captured by a cell-trapping matrix but are not lysed. In certain embodiments, DNA does not bind to a cell-trapping matrix in the presence of a cell wash buffer. Exemplary cell wash buffers include, but are not limited to, phosphate buffered saline (PBS); Tris-EDTA (TE), pH 7.5; Tris-Acetate-EDTA (TAE), pH 8.5); and Tris-Boric acid-EDTA (TBE), pH 8. In various embodiments, one skilled in the art can select a suitable cell wash buffer according to the selected cell-trapping matrix and cell types.

The term "compartment" refers to any containment structure that defines a discrete space configured to hold fluid. For example, a compartment may be a stand-alone container or receptacle that defines an interior space configured to hold fluid. Alternatively, a compartment may be one of a plurality of partitioned spaces within a container or receptacle, which is configured to hold fluid. In addition, the fluid-holding space defined by a compartment may be substantially enclosed or alternatively, open, at least partially, to atmosphere.

The term "differential extraction" refers to extraction methods utilized to extract a subset of cell types from a heterogeneous population of cells. In certain embodiments, differential extraction includes the selective lysis of sperm cells in a mixture of sperm cells and non-sperm cells, including, but not limited to, epithelial cells.

The term "DNA-binding particles" refers to magnetic particles that are capable of binding DNA under appropriate buffer conditions. Exemplary magnetic particles include, but are not limited to, ferromagnetic, paramagnetic, and superparamagnetic particles. In certain embodiments, DNA-binding particles bind DNA in the presence of a DNA-binding buffer.

The term "DNA-binding buffer" refers to a buffer in which DNA-binding particles and/or a cell-trapping matrix is capable of binding DNA.

The term "selective sperm lysis buffer" refers to a buffer that is capable of preferentially lysing sperm cells in a mixture comprising sperm cells and at least one type of non-sperm cells. Certain exemplary selective sperm lysis buffers are described, e.g., in U.S. Provisional Application Nos. 60/899,106 and 60/890,470. "Preferentially lysing sperm cells" means that primarily sperm cells are lysed. In certain embodiments, a negligible amount of non-sperm cells are lysed. In various embodiments, at least 80%, 85%, 90%, 95%, or 99% of the sperm cells are lysed. In various embodiments, at least 80%, 85%, 90%, or 95% of the non-sperm cells are not lysed.

The term "dilution buffer" refers to a buffer that can be used to dilute a selective sperm lysis buffer so that it becomes a DNA binding buffer. Dilution buffers may comprise, in various embodiments, a chaotropic salt, a monovalent salt, and/or an alcohol.

The term "elution buffer" refers to a buffer that releases DNA from DNA-binding particles and/or cell-trapping matrix. Certain exemplary elution buffers include, but are not limited to, low-salt buffers (including, but not limited to, TE and deionized water). In various embodiments, one skilled in the art can select a suitable elution buffer according to the DNA binding particles and/or cell-trapping matrix being used. In certain embodiments, heat is applied to facilitate elution of DNA in the presence of an elution buffer.

The term "forensic sample" refers to a biological sample obtained for use to address identity issues arising in legal contexts, including, but not limited to murder, rape, trauma, assault, battery, theft, burglary, other criminal matters, identity, parental or paternity testing, and mixed-up samples.

The term "general lysis buffer" refers to a buffer that lyses non-sperm cells and may or may not also lyse sperm cells. Certain exemplary general lysis buffers are known in the art, and in various embodiments, one skilled in the art can select a general lysis buffer based on the intended use. A nonlimiting exemplary general lysis buffer comprises 2% SDS, 20 mM EDTA, 200 mM NaCl, 20 mM Tris (pH8), and 500 μg/mL proteinase K.

The term "lysate" refers to a liquid phase with lysed cell debris and DNA.

The term "medical sample" refers to a sample obtained to address medical issues including, but not limited to research, diagnosis, and tissue and organ transplants.

The terms "salt" or "salt reagent" or "salt solution" refer to positively and/or negatively charged ionic reagents. In certain embodiments, a salt reagent disrupts sperm chromatin. A salt reagent may, in various embodiments, be a monovalent, bivalent, or multivalent ion. Exemplary salt reagents include, but are not limited to LiCl, NaCl, KCl. $Li_2SO_4$, $Na_2SO_4$, $K_2SO_4$, $MgCl_2$, $CaCl_2$, $MgSO_4$, $CaSO_4$, $NaNO_3$, $KNO_3$, $Mg(NO_3)_2$, and $Ca(NO_3)_2$.

The term "disulfide bond reducing agent" refers to an agent that reduces disulfide bonds, e.g., in proteins. In certain embodiments, a disulfide bond reducing agent disrupts protamine disulfide bridges in sperm cells. Disulfide bond reducing agents can be water-insoluble or water soluble. Exemplary water-insoluble agents include, but are not limited to, dithiothreitol (DTT) and Tris(2-carboxyethyl)phosphine hydrochloride (TCEP). Exemplary water-soluble agents include, but are not limited to, glutathione (GSH) and mercaptoethanol (ME).

Certain Exemplary Selective Sperm Lysis Buffers

In certain embodiments, a selective sperm lysis buffer comprises at least one disulfide bond reducing reagent and at least one salt reagent.

In certain embodiment, a disulfide bond reducing agent is selected from ME, DTT, GSH, and TCEP.

In certain embodiments, at least one salt reagent is selected from LiCl, NaCl, KCl. $Li_2SO_4$, $Na_2SO_4$, $K_2SO_4$, $MgCl_2$, $CaCl_2$, $MgSO_4$, $CaSO_4$, $NaNO_3$, $KNO_3$, $Mg(NO_3)_2$, and $Ca(NO_3)_2$. In certain embodiments, at least one salt reagent is selected from NaCl, KCl, and $MgCl_2$.

In certain embodiments, a selective sperm lysis buffer comprises at least one salt reagent at a concentration of at least 0.1M, 0.25M, 0.5M, 1M, 1.5M, or 2M. In certain embodiments, a selective sperm lysis buffer comprises at least one salt reagent at a concentration of between 0.1M and 2M.

In certain embodiments, a selective sperm lysis buffer comprises at least one disulfide bond reducing reagent at a concentration of at least 0.01M, 0.05M, 0.1M, 0.2M, 0.3M, 0.4M, 0.5M, 0.7M or 0.8M.

In certain embodiments, a selective sperm lysis buffer comprises at least one disulfide bond reducing reagent selected from ME, DTT, GSH, and TCEP and at least one salt reagent selected from NaCl, KCl, $MgCl_2$, and $CaCl_2$. In certain embodiments, the salt and reducing agent concentrations are such that the selective sperm lysis buffer will preferentially lyse sperm cells.

In certain embodiments, a selective sperm lysis buffer comprises NaCl. In certain embodiments, the NaCl concentration is at least 0.8M. In certain embodiments, a selective sperm lysis buffer comprises KCl. In certain embodiments, the KCl concentration is at least 0.8M. In certain embodiments, a selective sperm lysis buffer comprises $MgCl_2$. In certain embodiments, the $MgCl_2$ concentration is at least 0.25M. In certain embodiments, a selective sperm lysis buffer comprises DTT at a concentration of at least 50 mM.

In various embodiments, one of skill in the art can optimize the final salt concentration level to preferentially lyse sperm cells.

In certain embodiments, a selective sperm lysis buffer is diluted with a dilution buffer so that it becomes a DNA-binding buffer. In certain embodiments, a selective sperm lysis buffer is diluted with a DNA-binding buffer and the resulting buffer is a DNA-binding buffer. In various embodiments, one skilled in the art can select an appropriate dilution buffer and/or appropriate dilution amount in order to create a DNA-binding buffer or maintain the DNA-binding properties of a DNA binding buffer after mixing with a selective sperm lysis buffer.

Certain Exemplary Cell-Trapping Matrices and DNA-Binding Particles

A cell-trapping matrix is a matrix that captures cells, including but not limited to, sperm cells and epithelial cells. In certain embodiments, a cell-trapping matrix binds DNA under appropriate conditions, which conditions may be the same as, or different from, the conditions used to capture cells. In various embodiments, a cell-trapping matrix is comprised of magnetic particles. Exemplary magnetic particles include, but are not limited to, ferromagnetic, paramagnetic, and superparamagnetic particles.

Exemplary cell-trapping matrices and/or DNA-binding particles include, but are not limited to, porous silica beads with supermagnetic cores. Exemplary porous silica beads with supermagnetic cores include, but are not limited to, MP-50 (6.5 μm) and MP-85 (>8 μm) (W.R. Grace, Columbia, Md.); DNA IQ™ silica particles (Promega, Madison, Wis.); MagPrep® silica particles (Novagen, San Diego, Calif.); BcMag® silica-modified magnetic beads (5 μm or 1 μm) (Bioclone Inc., San Diego, Calif.); and supermagnetic silica particles (1 μm or 0.75 μm, G. Kisker GbR, Steinfurt, Germany). Certain exemplary non-silica cell-trapping matrices include, but are not limited to, iron oxide immobilized with streptavidin (Sigma, St. Louis, Mo.), iron(III) oxide powder (5 μm) (Sigma), MagMAX® magnetic particles (1 μm, Applied Biosystems, Foster City, Calif.); and Dynabeads® (Invitrogen, Carlsbad, Calif.), which may comprise different types of surface functional groups (e.g., Dynabeads® MyOne carboxylic acid beads, Dynabeads® WCX, Dynabeads® TALON, and Dynabeads® MyOne tosylactivated).

Certain Exemplary Methods of Cell Capture

In various embodiments, a cell-trapping matrix comprises magnetic particles. In certain embodiments, the cell-trapping matrix captures cells in the absence of a magnetic field. In certain embodiments, the cell-trapping matrix captures cells in the presence of a magnetic field. The timing and mechanism of cell capture depends, in various embodiments, on the cell-trapping matrix used and the buffer conditions.

A cell trapping matrix may capture cells by any of a variety of mechanisms. In certain embodiments, a cell-trapping matrix captures cells through a non-covalent interaction. Certain exemplary non-covalent interactions include, but are not limited to, hydrogen bonding, cation-π interactions, π-π interactions, ionic pairing, hydrophobic interactions, dipole-dipole interactions, dipole-induced dipole interactions, charge-dipole interactions, and van Der Waals interactions. In certain embodiments, cells are captured by the cell-trapping matrix through ionic interactions. In certain embodiments, cells are captured by the cell-trapping matrix through an antibody/antigen interaction.

In certain embodiments, the duration and strength of the non-covalent interaction is such that cells remain captured by the cell-trapping matrix while the matrix is moved from one location to another. In certain such embodiments, the cell-trapping matrix comprises magnetic particles and the movement is caused by applying a magnetic field. The type, duration and strength of a non-covalent association between cells and a cell-trapping matrix is determined, in various embodiments, by the size, shape, surface properties, surface morphologies, and/or density of the matrix; the size, shape, surface properties, surface morphologies, and/or density of the captured cells; and/or the composition, pH, and/or temperature of the buffer.

In certain embodiments, a cell-trapping matrix physically traps cells, e.g., when a magnetic field is applied. Such physical trapping may be, in certain embodiments, due to aggregation of cell-trapping matrix particles in the magnetic field. In certain embodiments, a cell-trapping matrix comprises irregularly shaped particles to facilitate such physical trapping of cells. In various embodiments, the cell-trapping matrix particles may be smaller or larger than the cells to be captured, or may be larger than some cells and smaller than other cells to be captured. In certain embodiments, the cell-trapping matrix may capture cells by pushing the cells towards the source of the magnetic field, sequestering them from the supernatant. In certain such embodiments, the cell-trapping matrix is comprised of particles at a density such that the spacing between particles is smaller than the size of the smallest cell in the sample.

In certain embodiments, more than one type of non-covalent interaction exists between cells and a cell-trapping matrix. In certain such embodiments, one type of non-covalent interaction may contribute more to cell capture, and which interaction predominates may vary from cell type to cell type in a sample.

Sperm cells have a diameter of about 5 μm, epithelial cells have a diameter of about 50μμ. In various embodiments, a cell-trapping matrix used to capture sperm cells and epithelial cells comprises particles with a diameter of between 0.5 μm and 100 μm. In certain embodiments, the particles have a diameter of between 1 μm and 10 μm. In certain embodiments, at least 85%, at least 90%, at least 95%, or at least 99% of the particles in a cell-trapping matrix have a diameter of between 0.5 μm and 100 μm, or between 1 μm and 10 μm. One skilled in the art can, in various embodiments, select the appropriate particles size, shape, density and surface properties for capturing cells according to the particular application.

In certain embodiments, a cell-trapping matrix comprises one or more antibodies. In certain such embodiments, one or more of the antibodies binds a cell surface antigen present on at least one type of cell in a sample. In certain embodiments, a cell-trapping matrix comprises one or more antibodies that together bind to at least one cell surface antigen on two or more cell types in a sample. As a non-limiting example, in certain embodiments, a cell-trapping matrix may comprise a first set of particles coated with an antibody that binds a cell-surface antigen on epithelial cells and a second set of particles coated with an antibody that binds a cell-surface antigen on sperm cells.

Certain exemplary antibodies that bind sperm cells and/or epithelial cells include, but are not limited to, monoclonal antibody BerEP4, which binds the human epithelial antigen, EpCAM (epithelial cell adhesion molecule); antibodies to sperm protamine; antibodies to carbohydrate epitope located on human sperm agglutination antigen-I (SAGA-I) (see, e.g., U.S. Pat. No. 5,605,803); antibodies to SPAN-X, a sperm protein present in nuclear vacuoles and sperm nuclear redundant membranes (see, e.g., PCT/US99/24973); antibodies to C58 or SMARC32 (see, e.g., U.S. Published App. 2002/0182751). In certain embodiments, an antibody binds a cell surface antigen (e.g., a protein or carbohydrate) present on multiple cell types.

In certain embodiments, cells are pushed, dragged, or carried by the cell-trapping matrix to the bottom of a compartment, when a magnetic field is applied underneath the compartment. In certain embodiments, cells are pushed, dragged, or carried by the cell-trapping matrix to the side of the compartment, when a magnetic field is applied from the side of the compartment. In certain embodiments, cells are pushed, dragged, or carried by the cell-trapping matrix to a magnetic bar inserted into the compartment. In certain such embodiments, the magnetic bar is covered, e.g., with a removable protectant to prevent contamination of the magnetic bar. In certain embodiments, the magnetic bar can be used to transfer the cell-trapping matrix from one compartment to another.

In certain embodiments, Dynabeads® MyOne Carboxylic Acid beads (Dynal Biotech) are used as a cell-trapping matrix to capture cells. The particles are 1 μm and are used, in certain embodiments, at a density of about $10^6$ particles/μl for a sample comprising about 55 cells/μL (e.g., 200 μL containing about 1000 sperm cells and about 10,000 epithelial cells). In certain embodiments, more that $10^6$ particles/μl can be used. In certain embodiments, fewer than $10^6$ particles/μl are used.

In various embodiments, at least 50%, at least 60%, at least 70%, at least 80%, at least 90%, or at least 95% of the intact cells in a sample are captured by the cell-trapping matrix. In various embodiments, after one cell type has been lysed, at least 50%, at least 60%, at least 70%, at least 80%, at least 90%, or at least 95% of the remaining intact cells in a sample are captured, or remain captured, by the cell-trapping matrix.

Certain Exemplary DNA-Binding Buffers

In certain embodiments, when the DNA-binding particles are silica beads, a DNA-binding buffer comprises a chaotropic salt. Certain exemplary chaotropic salts include, but are not limited to, guanidium isothiocyanate (GuSCN) and guanidium chloride. In certain embodiments, e.g., when the DNA-binding particles are non-silica beads, a DNA-binding buffer comprises a chaotropic salt and alcohol. In certain such embodiments, the DNA-binding buffer further comprises a monovalent salt. Certain exemplary monovalent salts include, but are not limited to, sodium acetate, sodium chloride, potassium acetate, potassium chloride, ammonium acetate, and ammonium chloride. Certain exemplary alcohols include, but are not limited to, isopropanol and ethanol. In certain embodiments, the alcohol is at a concentration of 30% or greater in the DNA-binding buffer. In certain embodiments, a DNA-binding buffer that comprises a chaotropic salt and an alcohol is referred to as a "DNA precipitation buffer." Certain exemplary DNA-binding buffers are described, e.g., in U.S. Pat. Nos. 5,234,809; 5,523,231; and 5,705,628. One skilled in the art can select a suitable DNA-binding buffer according to the DNA binding particles and/or cell-trapping matrix being used.

Exemplary DNA-binding buffers suitable for silica-based DNA-binding particles include, but are not limited to, BloodPrep™ DNA purification solution (Applied Biosystems) and DNA IQ™ Lysis Solution (Promega). In various embodiments, for non-silica DNA-binding particles, one skilled in the art can add a suitable amount of an alcohol to the BloodPrep™ DNA purification solution (Applied Biosystems) or the DNA IQ™ Lysis Solution (Promega). As a non-limiting example, in various embodiments, isopropanol is added to one of those solutions to a final concentration of 30% to create a DNA precipitation buffer. As a further non-limiting example, in various embodiments, ethanol is added to one of those solutions to a final concentration of 40-50% to create a DNA precipitation buffer.

In certain embodiments, DNA-binding particles are stored in DNA binding buffer in the systems described herein. In certain embodiments, DNA-binding particles are stored separately from a DNA-binding buffer in the systems described herein. DNA-binding particles are stored separately, in certain embodiments, when the DNA binding buffer is a DNA precipitation buffer.

In certain embodiments, non-sperm cells are lysed in a DNA-binding buffer. In certain embodiments, non-sperm cells are lysed in a DNA-binding buffer with the application of heat. In certain embodiments, when a DNA-binding buffer is a DNA precipitation buffer, non-sperm cells are first lysed in a DNA-binding buffer without the alcohol. In certain embodiments, alcohol is then added to the lysate to create the DNA precipitation buffer.

Certain Exemplary DNA Wash Buffers

In certain embodiments, a DNA wash buffers is formulated such that substantially no genomic DNA dissolves in the DNA wash buffer. In certain embodiments, a DNA wash buffers is formulated such that substantially no large DNA (e.g., greater than about 1 kb) dissolves in the DNA wash buffer. Certain exemplary DNA wash buffers are known in the art and generally comprise at least one alcohol. Certain exemplary alcohols that may be used in DNA wash buffers include, but are not limited to, ethanol and isopropanol.

In certain embodiments, when one DNA wash buffer is used, it comprises 90% ethanol. In certain embodiments, when the DNA is washed twice, the same DNA wash buffer is used for both washed. In certain embodiments, when the DNA is washed twice, two different DNA wash buffers are used. In certain embodiments, when two different DNA wash buffers are used, the second DNA wash buffer comprises a higher alcohol concentration than the first DNA wash buffer. In certain embodiments, a DNA wash buffer comprises GuSCN and/or GuCl. In certain embodiments, a DNA wash buffer comprises GuSCN and isopropanol. In certain embodiments, a DNA wash buffer comprises 70% ethanol. In certain embodiments, a DNA wash buffer comprises 90% ethanol.

In various embodiments, one skilled in the art can formulate one or more DNA wash buffers according to the selected application.

Certain Exemplary Methods of DNA Analysis

After the DNA has been isolated, various methods can be used for DNA analysis, such as Restriction Fragment Length Polymorphism (RFLP) analysis, and various Polymerase Chain Reaction (PCR)-based methods, including, but not limited to, Short Tandem Repeat (STR) analysis.

Polymerase Chain Reaction (PCR) refers to a reaction that can be used to amplify nucleic acids, including, but not limited to, small amounts of DNA. PCR is a technique in which cycles of denaturation, annealing with one or more primers, and extension with one or more DNA polymerases, are used to create additional copies of a target DNA. In certain embodiments, PCR amplifies the DNA sequence by more than $10^6$ fold. Certain exemplary methods of PCR are described, e.g., in U.S. Pat. Nos. 4,683,195; 4,965,188; and 4,683,202; and European Patent Nos. EP 201184 and EP 200362.

In certain embodiments, DNA samples are subjected to PCR amplification using primers specific for each locus that contains, e.g., an STR of interest. An STR locus is composed of tandemly repeated sequences, each of which is, e.g., 2 to 7 bp in length. In various embodiments, loci containing 4 bp (tetranucleotide) and/or 5 bp repeat sequences are used for human identification. Four and 5 bp repeat sequences are found throughout the human genome and are, in certain instances, highly polymorphic. The number of alleles at a tetranucleotide repeat STR locus ranges, in various embodiments, from about 4 to 20.

In certain embodiments, when isolated DNA is used for detection of polymorphic STRs, the amplified alleles from the individual DNA samples can be compared to one or more size standards, e.g., commercial DNA markers and/or locus-specific allelic ladders, to determine the alleles present at each locus. In certain embodiments, allelic ladders comprise two or more distinct lengths of DNA representing two or more known alleles from a particular locus. In various embodiments, DNA may be visualized by any technique, including, but not limited to, silver staining, radioactive labeling, fluorescent labeling, various dyes and stains. In certain embodiments, prior to visualization, DNA is separated using denaturing or native gel electrophoresis, or any other size separation method.

In certain embodiments, amplified alleles are subjected to DNA sequence analysis.

Certain exemplary methods of DNA amplification and analysis are known in the art and are described, e.g., in Budowle et al. (DNA Typing Protocols: Molecular Biology and Forensic Analysis, Eaton Publishing: MA, USA (2000)).

Certain Exemplary Magnetic Particle Handling Instruments

In certain embodiments, a differential extraction system comprises a magnetic particle handling instrument and a removable cartridge comprising a plurality of compartments, wherein at least one of the compartments comprises at least one reagent used in the differential extraction system.

In certain embodiments, a magnetic particle handling instrument is similar to the BioRobot EZ1 Workstation (Qiagen). See, e.g., EZ1 DNA Handbook, Second Edition (February 2004) (Qiagen). The BioRobot EZ1 Workstation comprises a stage capable of moving in a plane parallel to the floor, a pipette capable of moving upwards and downwards relative to the stage, and a magnet capable of moving towards and away from the pipette. The BioRobot EZ1 Workstation is able to move both magnetic particles and liquids between compartments. In certain instances, the BioRobot EZ1 Workstation functions as follows. A removable cartridge containing a plurality of compartments comprising a plurality of liquid reagents is placed on the stage of the BioRobot EZ1 Workstation. The removable cartridge also comprises at least one compartment containing magnetic particles. The stage moves the compartment containing the magnetic particles to a position beneath the pipette. The pipette lowers into the compartment and sucks up a liquid solution containing the magnetic particles. The magnet moves toward the pipette to hold the magnetic particles inside the pipette while the pipette expels the liquid solution without the magnetic particles. The stage then moves a second compartment containing a reagent to a position beneath the pipette containing the magnetic particles held by the magnet. The pipette sucks up the reagent from the second compartment, the magnet moves away from the pipette and the pipette expels the reagent and the magnetic particles into the second compartment.

In certain embodiments, a magnetic particle handling instrument is similar to the Maxwell 16 Instrument (Promega). See, e.g., Maxwell 16 Instrument Operating Manual (September 2005) (Promega). The Maxwell 16 Instrument comprises a stage capable of moving in a plane parallel to the floor, a plunger capable of moving upwards and downwards relative to the stage, and a magnet located inside of the plunger and capable of moving upwards and downwards relative to the end of the plunger. The Maxwell 16 Instrument is able to move magnetic particles, but not liquids, between compartments. In certain instances, the Maxwell 16 Instrument functions as follows. A removable cartridge containing a plurality of compartments comprising a plurality of liquid reagents is placed on the stage of the Maxwell 16 Instrument. The removable cartridge also comprises at least one compartment containing magnetic particles. The stage moves the compartment containing the magnetic particles to a position beneath the plunger. The plunger pipette lowers into the compartment and the magnet lowers within the plunger to attract the magnetic particles to the end of the plunger. The plunger and magnet then rise, and the stage moves a second compartment containing a reagent to a position beneath the plunger with the magnetic particles held by the magnet. The plunger lowers into the second compartment and the magnet rises away from the end of the plunger, releasing the magnetic particles into the second compartment.

In certain embodiments, a magnetic particle handling instrument comprises a stage capable of moving in a plane parallel to the floor, a pipette capable of moving upwards and downwards relative to the stage, and a magnet in a location allowing it to contact a cartridge placed on the stage. In various embodiments, a magnet may be located beneath the cartridge or on one or multiple sides of the cartridge. In certain embodiments, the magnet is capable of moving towards and away from the cartridge in order to exert and release a magnetic force on at least one compartment of the cartridge. In certain embodiments, the magnet is stationery and can be turned on and off electronically in order to exert and release a magnetic force on at least one compartment of the cartridge. Such an exemplary magnetic particle handling instrument functions as follows. A removable cartridge containing a plurality of compartments comprising a plurality of liquid reagents is placed on the stage of the instrument. The removable cartridge also comprises at least one compartment containing magnetic particles. The stage moves a compartment containing a reagent to a position beneath the pipette. The pipette sucks up the reagent and the stage moves the compartment containing the magnetic particles to a position beneath the pipette. The pipette then expels the reagent into the compartment. The magnet attracts the magnetic particles to one location within the compartment, away from the pipette, and the pipette then sucks up the liquid without the magnetic particles. In this manner, the pipette can be used to bring reagents to the magnetic particles and remove reagents from the magnetic particles, while a magnet is used to hold the magnetic particles out of the way of the pipette.

In various embodiments, one skilled in the art can design and/or program an instrument to carry out the methods described herein. In certain embodiments, such an instrument may be similar to one or more of the instruments described above.

Certain Exemplary Systems and Methods for Differential Extraction

In various embodiments, a system for differential extraction comprises a cartridge comprising a plurality of compartments, wherein at least one of the compartments comprises a selective sperm lysis buffer. Certain exemplary systems and methods for differential extraction are described herein. In certain embodiments, the method comprises transferring fluids between compartments. In certain embodiments, the method comprises transferring DNA-binding particles between compartments. In certain embodiments, the method comprises transferring fluids and DNA-binding particles between compartments.

The following examples of differential extraction systems are non-limiting. For example, the arrangement of compartments shown in the Figures and described herein is figurative and non-limiting. In various embodiments one skilled in the art can design a system based on the teachings herein, the intended use, and the selected instrumentation. In various embodiments, such a system comprises more or fewer compartments than any of the following exemplary systems described herein. In various embodiments, such a system separates reagents into separate compartments that are shown combined in one or more of the following exemplary systems.

Certain Exemplary Systems and Methods Using Fluid Transfer Between Compartments

FIG. 1 shows a first non-limiting exemplary system for differential extraction of sperm cells and non-sperm cells, e.g., epithelial cells, according to certain embodiments. The system shown in FIG. 1 is used, for example, when a sample comprises an excess of non-sperm cells relative to sperm cells (e.g., at least 10-fold more non-sperm cells than sperm cells). The system of FIG. 1 does not lyse the non-sperm cells, but instead collects residual DNA present in the sample after cell capture on the cell-trapping matrix. Such residual DNA may be present due to cell breakage prior to placing the sample in the system. Such cell breakage may occur, in various embodiments, prior to collection, during collection, during storage, during transport, and/or during transfer of the sample from one container to another. Because of the excess of non-sperm cells relative to sperm-cells in the sample, the residual DNA comprises an excess of non-sperm cell DNA relative to sperm cell DNA.

In embodiments depicted in FIG. 1, a sample comprising a mixture of sperm cells and non-sperm cells is placed in compartment 1. Compartment 1 comprises a cell-trapping matrix, which captures the sperm cells and the non-sperm cells. The supernatant from compartment 1 is then removed to a collection vessel (not shown). If the original sample contained an excess of non-sperm cells, e.g., epithelial cells, relative to sperm cells (for example, more than 10-fold more non-sperm cells than sperm cells), the supernatant from the sample binding may contain sufficient non-sperm cell DNA for analysis.

A cell wash buffer located in compartment 2 is then transferred to compartment 1. The cell wash supernatant from compartment 1 is then transferred to a waste receptacle, which is shown as compartment 0. The waste receptacle may or may not be a contiguous part of the system shown in FIG. 1. In certain embodiments, when the compartments 1 through 6 of FIG. 1 are contained in a cartridge, the waste compartment 0 is not part of the cartridge. In certain embodiments, a cartridge comprises compartments 0 through 6 of FIG. 1.

After removal of the cell wash supernatant from compartment 1, a selective sperm lysis buffer is transferred from compartment 3 to compartment 1. The selective sperm lysis buffer lyses the sperm cells bound to the cell-trapping matrix in compartment 1. Following lysis of the sperm cells, the lysate supernatant is transferred from compartment 1 to compartment 4, which contains DNA-binding particles and a dilution buffer, which, when combined with the selective sperm lysis buffer, forms a DNA-binding buffer. Following DNA binding, the supernatant from compartment 4 is transferred to the waste compartment 0. A DNA wash buffer is then transferred from compartment 5 to compartment 4. The DNA wash buffer supernatant is then transferred from compartment 4 to the waste compartment 0.

In certain embodiments, a second DNA wash buffer is contained in a compartment 7 (not shown in FIG. 1). In certain such embodiments, the second DNA wash buffer is then transferred to compartment 4. The second DNA wash buffer supernatant is then transferred from compartment 4 to the waste compartment 0.

Finally, an elution buffer is transferred from compartment 6 to compartment 4. The elution buffer releases sperm cell DNA from the DNA-binding particles into the elution supernatant. In certain embodiments, the elution buffer is heated to facilitate elution of the bound DNA. In certain embodiments, the elution supernatant may then transferred from compartment 4 to a second collection vessel (not shown in FIG. 1). The sperm cell DNA can then be subjected to DNA analysis.

FIG. 2 shows a second non-limiting exemplary system for differential extraction of sperm cells and non-sperm cells, e.g., epithelial cells, according to certain embodiments. In the system shown in FIG. 2, the cell-trapping matrix also serves as the DNA-binding matrix for the non-sperm cell DNA.

In embodiments depicted in FIG. 2, a sample comprising a mixture of sperm cells and non-sperm cells is placed in compartment 1. Compartment 1 comprises a cell-trapping matrix, which captures the sperm cells and the non-sperm cells. The supernatant from compartment 1 is then transferred to a waste receptacle, which is shown as compartment 0. The waste receptacle may or may not be a contiguous part of the system shown in FIG. 2. In certain embodiments, when the compartments 1 through 7 of FIG. 2 are contained in a cartridge, the waste compartment 0 is not part of the cartridge. In certain embodiments, a cartridge comprises compartments 0 through 7 of FIG. 2.

A cell wash buffer located in compartment 2 is then transferred to compartment 1. The cell wash supernatant from compartment 1 is then transferred to a waste receptacle, which is shown as compartment 0. After removal of the cell wash supernatant from compartment 1, a selective sperm lysis buffer is transferred from compartment 3 to compartment 1. The selective sperm lysis buffer lyses the sperm cells captured by the cell-trapping matrix in compartment 1. Following lysis of the sperm cells, the lysate supernatant is transferred from compartment 1 to compartment 5, which contains DNA-binding particles and a dilution buffer, which, when combined with the selective sperm lysis buffer, forms a DNA-binding buffer. A DNA binding buffer is then transferred from compartment 4 to compartment 1, which now contains non-sperm cells captured by the cell-trapping matrix. The DNA-binding buffer is incubated with the cell-trapping matrix for five minutes with heating to about 70° C. (heating element not shown in FIG. 2) to lyse the non-sperm cells, e.g., epithelial cells. The heating element is, in certain embodiments, part of a fluid handling or magnetic particle handling instrument. Non-sperm cell DNA binds to the cell-trapping matrix in the DNA binding buffer.

Following DNA binding in compartments 1 and 5, the supernatants from compartments 1 and 5 are transferred to the waste compartment 0. A DNA wash buffer is then transferred from compartment 6 to each of compartments 1 and 5. The DNA wash buffer supernatant is then transferred from compartments 1 and 5 to the waste compartment 0.

In certain embodiments, a second DNA wash buffer is contained in a compartment 8 (not shown in FIG. 2). In certain such embodiments, the second DNA wash buffer is then transferred to compartments 1 and 5. The second DNA wash buffer supernatant is then transferred from compartments 1 and 5 to the waste compartment 0.

Finally, an elution buffer is transferred from compartment 7 to each of compartments 1 and 5. The elution buffer releases sperm cell DNA from the DNA-binding particles into the elution supernatant in compartment 5 and releases non-sperm cell DNA from the DNA-binding particles into the elution supernatant in compartment 1. In certain embodiments, the elution buffer is heated to facilitate elution of the bound DNA. In certain embodiments, the elution supernatant is then transferred from compartment 5 to a collection vessel (not shown in FIG. 3). The sperm cell DNA can then be subjected to DNA analysis. In certain embodiments, the elution supernatant is then transferred from compartment 1 to a second collection vessel (not shown in FIG. 3). The non-sperm cell DNA can then be subjected to DNA analysis.

FIG. 3 shows a third non-limiting exemplary system for differential extraction of sperm cells and non-sperm cells, e.g., epithelial cells, according to certain embodiments. The system shown in FIG. 3 comprises two separate compartments containing DNA-binding particles, one of which is used to bind sperm cell DNA and one of which is used to bind non-sperm cell DNA.

In embodiments depicted in FIG. 3, a sample comprising a mixture of sperm cells and non-sperm cells is placed in compartment 1. Compartment 1 comprises a cell-trapping matrix, which captures the sperm cells and the non-sperm cells. The supernatant from compartment 1 is then transferred to a waste receptacle, which is shown as compartment 0. The waste receptacle may or may not be a contiguous part of the system shown in FIG. 3. In certain embodiments, when the compartments 1 through 7 of FIG. 3 are contained in a cartridge, the waste compartment 0 is not part of the cartridge. In certain embodiments, a cartridge comprises compartments 0 through 7 of FIG. 3.

A cell wash buffer located in compartment 2 is then transferred to compartment 1. The cell wash supernatant from compartment 1 is then transferred to a waste receptacle, which is shown as compartment 0. After removal of the cell wash supernatant from compartment 1, a selective sperm lysis buffer is transferred from compartment 3 to compartment 1. The selective sperm lysis buffer lyses the sperm cells captured by the cell-trapping matrix in compartment 1. Following lysis of the sperm cells, the lysate supernatant is transferred from compartment 1 to compartment 5, which contains DNA-binding particles and a dilution buffer, which, when combined with the selective sperm lysis buffer, forms a DNA-binding buffer. A DNA binding buffer is then transferred from compartment 4 to compartment 1, which now contains non-sperm cells captured by the cell-trapping matrix. While transferring the DNA-binding buffer from compartment 4, in certain embodiments, the DNA-binding particles are held in compartment 4 by a magnet on the fluid handling instrument, to prevent the DNA-binding particles from being removed with the DNA-binding buffer. The DNA-binding buffer is incubated with the cell-trapping matrix for five minutes with heating to about 70° C. (heating element not shown in FIG. 3) to lyse the non-sperm cells, e.g., epithelial cells. The heating element is, in certain embodiments, part of a fluid handling or particle handling instrument. The DNA-binding buffer/lysate supernatant is then transferred from compartment 1 back to compartment 4, which contains DNA-binding particles.

Following DNA binding in compartments 4 and 5, the supernatants from compartments 4 and 5 are transferred to the waste compartment 0. A DNA wash buffer is then transferred from compartment 6 to each of compartments 4 and 5. The DNA wash buffer supernatant is then transferred from compartments 4 and 5 to the waste compartment 0.

In certain embodiments, a second DNA wash buffer is contained in a compartment 8 (not shown in FIG. 3). In certain such embodiments, the second DNA wash buffer is then transferred to compartments 4 and 5. The second DNA wash buffer supernatant is then transferred from compartments 4 and 5 to the waste compartment 0.

Finally, an elution buffer is transferred from compartment 7 to each of compartments 4 and 5. The elution buffer releases sperm cell DNA from the DNA-binding particles into the elution supernatant in compartment 5 and releases non-sperm cell DNA from the DNA-binding particles into the elution supernatant in compartment 4. In certain embodiments, the elution buffer is heated to facilitate elution of the bound DNA. In certain embodiments, the elution supernatant may then transferred from compartment 5 to a collection vessel (not shown in FIG. 3). The sperm cell DNA can then be subjected to DNA analysis. In certain embodiments, the elution supernatant may then transferred from compartment 4 to a second collection vessel (not shown in FIG. 3). The non-sperm cell DNA can then be subjected to DNA analysis.

In certain embodiments, a dilution buffer and/or a DNA-binding buffer is kept separate from DNA-binding particles in a system until the DNA-binding reaction is carried out. Keeping such components separate may be desirable, in certain embodiments, when the dilution buffer or DNA-binding buffer comprises alcohol. One skilled in the art can modify any of the systems of FIGS. 1 to 3 to keep the DNA-binding particles separate from the dilution and/or DNA-binding buffer until the DNA-binding reaction is carried out.

In certain embodiments, a magnetic force is applied to the cell-trapping matrix to facilitate cell trapping. The magnetic force is applied, in certain embodiments, by an instrument portion of the differential extraction system.

Certain Exemplary Systems and Methods Using Transfer of DNA-Binding Particles Between Compartments FIG. 4 shows a fourth non-limiting exemplary system for differential extraction of sperm cells and non-sperm cells, e.g., epithelial cells, according to certain embodiments. The system shown in FIG. 4 is designed for a magnetic particle-handling instrument that is also able to move liquid between compartments. See, e.g., the BioRobot EZ1 Workstation (Qiagen). The system shown in FIG. 4 processes sperm cell DNA in compartments 3 to 6 and non-sperm cell DNA in compartments 7 to 9. The cell-trapping matrix also serves as the DNA-binding matrix for the non-sperm cell DNA in the exemplary system shown in FIG. 4. The cell-trapping matrix in that system is magnetic.

In embodiments depicted in FIG. 4, a sample comprising a mixture of sperm cells and non-sperm cells is placed in compartment 1. Compartment 1 comprises a cell-trapping matrix, which captures the sperm cells and the non-sperm cells. The cell-trapping matrix is transferred to compartment 2, which contains a cell wash buffer. The cell-trapping matrix is then transferred to compartment 3, which contains a selective sperm lysis buffer. The selective sperm lysis buffer lyses the sperm cells captured by the cell-trapping matrix. After lysis of the sperm cells, the cell-trapping matrix, which still has captured non-sperm cells, is transferred to the DNA-binding buffer in compartment 7. The DNA-binding buffer in compartment 7 is incubated with the cell-trapping matrix for five minutes with heating to about 70° C. (heating element not shown in FIG. 4) to lyse the non-sperm cells, e.g., epithelial cells. The heating element is, in certain embodiments, part of a fluid handling or particle handling instrument. The non-sperm cell DNA binds to the cell-trapping matrix in the DNA binding buffer. The cell-trapping matrix with the bound non-sperm cell DNA is then transferred to compartment 8, which contains a DNA wash buffer. Finally, the cell-trapping matrix with the bound non-sperm cell DNA is transferred to compartment 9, which contains an elution buffer. In certain embodiments, the elution buffer is heated to facilitate elution of the bound DNA. In certain embodiments, the elution supernatant may then transferred from compartment 9 to a collection vessel (not shown in FIG. 4). The non-sperm cell DNA can then be subjected to DNA analysis.

The selective sperm lysis buffer supernatant in compartment 3 is transferred to compartment 4, which contains DNA-binding particles and a dilution buffer, which, when combined with the selective sperm lysis buffer, forms a DNA-binding buffer. The DNA-binding particles with the bound sperm cell DNA are then transferred to compartment 5, which contains a DNA wash buffer. Finally, the DNA-binding particles with the bound sperm cell DNA are transferred to compartment 6, which contains an elution buffer. In certain embodiments, the elution buffer is heated to facilitate elution of the bound DNA. In certain embodiments, the elution supernatant may then transferred from compartment 6 to a second collection vessel (not shown in FIG. 4). The sperm cell DNA can then be subjected to DNA analysis.

In certain embodiments, a second DNA wash buffer is contained in a compartment 10 and in a compartment 11 (not shown in FIG. 4). In certain such embodiments, the cell-trapping matrix with the bound non-sperm cell DNA is transferred to compartment 10, which contains a second DNA wash buffer, prior to being transferred to the elution compartment. In certain such embodiments, the DNA-binding matrix with the bound sperm cell DNA is transferred to compartment 11, which contains a second DNA wash buffer, prior to being transferred to the elution compartment.

FIG. 5 shows a fifth non-limiting exemplary system for differential extraction of sperm cells and non-sperm cells, e.g., epithelial cells, according to certain embodiments. The system shown in FIG. 5 is designed for a magnetic particle-handling instrument that cannot also able to move liquid between compartments. See, e.g., the Maxwell 16 Instrument (Promega). The system shown in FIG. 5 processes sperm cell DNA in compartments 3 to 5 and non-sperm cell DNA in compartments 6 to 8. The cell-trapping matrix also serves as the DNA-binding matrix for the non-sperm cell DNA in the exemplary system shown in FIG. 5. The cell-trapping matrix in that system is magnetic.

In embodiments depicted in FIG. 5, a sample comprising a mixture of sperm cells and non-sperm cells is placed in compartment 1. Compartment 1 comprises a cell-trapping matrix, which captures the sperm cells and the non-sperm cells. The cell-trapping matrix is transferred to compartment 2, which contains a cell wash buffer. The cell-trapping matrix is then transferred to compartment 3. Compartment 3 in FIG. 5 comprises two sections that are partitioned from one another. The partition between the sections is breakable by the magnetic particle handling instrument, e.g., by physical force. The top portion of compartment 3 comprises a selective sperm lysis buffer. The bottom portion of compartment 3, which is partitioned from the top portion, contains DNA-binding particles and a dilution buffer. The cell-trapping matrix is transferred into the top portion initially. The selective sperm lysis buffer lyses the sperm cells captured by the cell-trapping matrix. After lysis of the sperm cells, the cell-trapping matrix, which is still has captured non-sperm cells, is transferred to the DNA-binding buffer in compartment 6. The DNA-binding buffer is incubated with the cell-trapping matrix for five minutes with heating to about 70° C. (heating element not shown in FIG. 5) to lyse the non-sperm cells, e.g., epithelial cells. The heating element is, in certain embodiments, part of a fluid handling or particle handling instrument. The non-sperm cell DNA binds to the cell-trapping matrix in the DNA binding buffer. The cell-trapping matrix with the bound non-sperm cell DNA is then transferred to compartment 7, which contains a DNA wash buffer. Finally, the cell-trapping matrix with the bound non-sperm cell DNA is transferred to compartment 8, which contains an elution buffer. In certain embodiments, the elution buffer is heated to facilitate elution of the bound DNA. In certain embodiments, the elution supernatant may then transferred from compartment 8 to a collection vessel (not shown in FIG. 5). The non-sperm cell DNA can then be subjected to DNA analysis.

After the cell-trapping matrix is removed, the instrument breaks the breakable partition between the top portion compartment 3 and the bottom portion of compartment 3 to mix the selective sperm lysis buffer supernatant with the DNA-binding particles and the dilution buffer, which, when combined with the selective sperm lysis buffer, forms a DNA-binding buffer. The DNA-binding particles with the bound sperm cell DNA are then transferred to compartment 4, which contains a DNA wash buffer. Finally, the DNA-binding particles with the bound sperm cell DNA are transferred to compartment 5, which contains an elution buffer. In certain embodiments, the elution buffer is heated to facilitate elution of the bound DNA. In certain embodiments, the elution supernatant is then transferred from compartment 5 to a second collection vessel (not shown in FIG. 5). The sperm cell DNA can then be subjected to DNA analysis.

In certain embodiments, a second DNA wash buffer is contained in a compartment 9 and in a compartment 10 (not shown in FIG. 5). In certain such embodiments, the cell-trapping matrix with the bound non-sperm cell DNA is transferred to compartment 9, which contains a second DNA wash buffer, prior to being transferred to the elution compartment. In certain such embodiments, the DNA-binding matrix with the bound sperm cell DNA is transferred to compartment 10, which contains a second DNA wash buffer, prior to being transferred to the elution compartment.

FIG. 6 shows a system similar to the system of FIG. 5, except the DNA-binding particles used to bind the sperm cell DNA are kept in a separate compartment (compartment 4) from the dilution buffer, according to certain embodiments. In embodiments depicted in FIG. 6, compartment 3 has two separate sections separated by a breakable seal, similar to compartment 3 of the system of FIG. 5. In embodiments depicted in FIG. 6, however, the lower compartment contains only the dilution buffer, so when the instrument breaks the seal, the selective sperm lysis buffer and the dilution buffer form a DNA-binding buffer. The instrument then transfers the DNA-binding particles from compartment 4 to compartment 3 to bind the sperm cell DNA.

In certain embodiments, a dilution buffer or a DNA-binding buffer is kept separate from DNA-binding particles in a system until the DNA-binding reaction is carried out. Keeping such components separate may be desirable, in certain embodiments, when the dilution buffer or DNA-binding buffer comprises alcohol. In various embodiments, one skilled in the art can modify any of the systems of FIGS. 3 to 6 to keep the DNA-binding particles separate from the dilution and/or DNA-binding buffer until the DNA-binding reaction is carried out.

In certain embodiments, a system comprises one or more empty compartments. One or more empty compartments may be used, in certain embodiments, as a location to dry the DNA-binding particles, e.g., after a wash and before elution.

What is claimed:

1. A method comprising:
    (a) placing a biological sample in a first compartment of a system, wherein the first compartment comprises a cell-trapping matrix, wherein the compartment is exposed to a magnetic force external to the compartment;
    (b) capturing the sperm cells and the non-sperm cells with the cell-trapping matrix;
    (c) incubating the cell-trapping matrix and the captured sperm cells and non-sperm cells in a selective sperm lysis buffer to form a sperm cell lysate, the selective sperm lysis buffer comprising about 1 M KCl and 200 mM DTT;
    (d) binding sperm cell DNA from the sperm cell lysate to a plurality of DNA-binding particles; and
    (e) eluting the sperm cell DNA from the DNA-binding particles.

2. The method of claim 1, wherein the capturing the sperm cells and the non-sperm cells with the cell-trapping matrix comprises applying a Magnetic force to the cell-trapping matrix.

3. The method of claim 1, wherein the incubating the cell-trapping matrix and the captured sperm cells and non-sperm cells in a selective sperm lysis buffer occurs in the first compartment of system.

4. The method of claim 3, wherein the binding the sperm cell DNA to a plurality of DNA-binding particles occurs in a second compartment of the system.

5. The method of claim 4, wherein the eluting the sperm cell DNA from the DNA-binding particles occurs in the second compartment of the system.

6. The method of claim 4, wherein the sperm cell lysate is moved from the first compartment to the second compartment.

7. The method of claim 1, wherein the incubating the cell-trapping matrix and the captured sperm cells and non-sperm cells in a selective sperm lysis buffer occurs in a second compartment of the system.

8. The method of claim 7, wherein the binding the sperm cell DNA to a plurality of DNA-binding particles occurs in a second compartment of the system.

9. The method of claim 8, wherein the eluting the sperm cell DNA from the DNA-binding particles occurs in a third compartment of the system.

10. The method of claim 7, wherein the cell-trapping matrix and the captured sperm cells and non-sperm cells are moved from the first compartment to the second compartment using a magnetic force.

11. The method of claim 1, wherein the non-sperm cells remain captured on the cell-trapping matrix after incubating the cell-trapping matrix in the selective sperm lysis buffer.

12. The method of claim 11, wherein the non-sperm cells are lysed and the non-sperm cell DNA is bound to the cell-trapping matrix.

13. The method of claim 11, wherein the non-sperm cells are lysed and the non-sperm cell DNA is bound to a second plurality of DNA-binding particles.

14. A kit comprising: a multi-compartment container, wherein at least one compartment is exposed to a magnetic force external to the compartment and wherein at least one compartment comprises a selective sperm lysis buffer, the selective sperm lysis buffer comprising about 1 M KCl and 200 mM DTT.

15. The kit for differential extraction of sperm cells of claim 14, wherein at least one compartment of the multi-compartment container comprises a cell-trapping matrix.

16. The kit for differential extraction of sperm cells of claim 14, wherein at least one compartment of the multi-compartment container comprises a plurality of DNA-binding particles.

17. The kit for differential extraction of sperm cells of claim 14, wherein at least one compartment of the multi-compartment container comprises an elution buffer.

18. The kit for differential extraction of sperm cells of claim 14,
wherein the multi-compartment container comprises:
a first compartment comprising a cell-trapping matrix;
a second compartment comprising a cell wash buffer;
a third compartment comprising the selective sperm lysis buffer;
a fourth compartment comprising a plurality of DNA binding particles;
a fifth compartment comprising a DNA wash buffer; and
a sixth compartment comprising an elution buffer.

* * * * *